United States Patent [19]

Helmberger et al.

[11] 4,066,355

[45] Jan. 3, 1978

[54] SOLID-STATE COLOR-COPYING SCANNER

[75] Inventors: Josef Helmberger, Munich; Klaus Stadler, Irschenhausen, both of Germany

[73] Assignee: AGFA-Gevaert, AG, Leverkusen, Germany

[21] Appl. No.: 674,632

[22] Filed: Apr. 7, 1976

[30] Foreign Application Priority Data

Apr. 9, 1975 Germany .................. 2515501

[51] Int. Cl.$^2$ ............................................. G03B 27/78
[52] U.S. Cl. ..................................... 355/38; 250/208;
250/226; 355/4; 355/77; 358/78
[58] Field of Search ............................. 355/4, 38, 77;
356/175-178; 358/6, 9, 78, 80; 250/208, 226

[56] References Cited

U.S. PATENT DOCUMENTS

| 3,120,782 | 2/1964 | Goddard et al. | 355/38 X |
| 3,519,347 | 7/1970 | Bowker et al. | 355/38 X |
| 3,801,197 | 4/1974 | Akiyama et al. | 355/38 X |
| 3,829,214 | 8/1974 | Zahn et al. | 355/38 X |
| 3,904,816 | 9/1975 | Taudt et al. | 358/80 X |
| 3,944,726 | 3/1976 | Ito | 358/78 X |
| 3,947,110 | 3/1976 | Yamada | 355/38 |
| 3,975,761 | 8/1976 | Taudt et al. | 355/78 |

Primary Examiner—Richard A. Wintercorn
Attorney, Agent, or Firm—Michael J. Striker

[57] ABSTRACT

An original bearing a multicolor image is displaced in a transverse direction passed a scanning location and a strip extending transverse to this direction on the original is irradiated with a white light for a predetermined time period. During this time period a plurality of different color-component strips are optically derived each corresponding to a respective color component of the irradiated strip and each of these color component strips is applied to a respective solid-state transducer. A row of photodiodes in the transducer charges up respective capacitors therein during the scanning time period and the charges in these capacitors are read out seriatim and fed to respective scribers which reproduce the respective color component of the image on the original on the copy sheet. Dichroic mirrors tippable about axes parallel to the irradiated strip on the original are employed to pick off the separate color components.

10 Claims, 2 Drawing Figures

SOLID-STATE COLOR-COPYING SCANNER

CROSS-REFERENCE RELATED APPLICATIONS

This application is related to copending and commonly assigned patent applications Ser. Nos. 614,786 and 615,795 filed Sept. 19. 1975 and Spet. 22, 1975, respectively.

BACKGROUND OF THE INVENTION

The present invention relates to a method of and apparatus for color-copying. More particularly this invention concerns a scanning method and apparatus for a color-copying system.

A color-copying method is known wherein the original is irradiated with a white light and several color components are derived from the irradiated portion of the original. Each of these color components is applied to a separate light-sensitive element and converted thereby into corresponding electrical signals.

When the scanning is done in a line-by-line fashion as described in the above-cited copending patent applications, each line or strip on the original is broken down into a multiplicity of spots or sections. Each color-component line is read by a device working in accordance with the principle of an iconoscope, a orthicon, or a vidicon. Such devices all use a scanning electron beam which is caused to pass over the line being scanned so as to produce a succession of electrical signals each of whose amplitude is proportional to the intensity of the respective color of light at the respective section. The mosaic arrangement in such a pickup or transducer device inherently separates the band or strip into a succession of sections.

The application of such an arrangement to color-copying, however, presents a considerable amount of difficulty. Since each color-component strip must be scanned by a respective light spot or electron beam is of frequently very low intensity, it is necessary to set the transducer up for maximum sensitivity. This has the frequent result of overloading it so that the device is ruined and the expensive pickup device must be replaced. Alternately it is possible to reduce scanning speed so that the electron beam or light spot rests a relatively long period of time on each section, but this has the concomitant disadvantage of greatly increasing copy time.

When the copy is produced electrophotographically the separate color components must be applied at different times to the copy sheet, with developing and fixing of each color component before application of the next one. Proper electronic masking of the color components is only possible when all of the color components are scanned at the same time. Thus, the scanning for each color component requires a three-channel scanner. The other color components are scribed on the copy sheet after the first component. When three-channel scanning is used, it is therefore necessary to store all of the color component signals. With the picture having dimensions of 90 by 120 mm with 10 lines/mm each color component requires $1.08 \times 10^6$ places in the memory for the analog signals. For an analog/digital conversion it is necessary to take into account 128 gray levels. Thus, the memory must have a capacity of $1.08 \times 10^6$ words each of 7 bits. At a scanning rate of three images per second the analog/digital and digital/analog conversion must operate with a scanning frequency of approximately 4 MHz.

For this reason it is frequently considered necessary to use a separate scanner for each scriber. This eliminates the need for an enormous memory capacity but brings up the problem of registration. The three or four scanning tubes must be controlled so that the individual color components register exactly with one another on the copy sheet. Even if the images are shifted by so much as a few line sections relative to each other, even as few as two or three per thousand, the copy can be unusable.

SUMMARY OF THE INVENTION

It is therefore an object of the present invention to provide an improved color-copying method and apparatus.

Another object is the provision of a color-copying arrangement which overcomes the above-given disadvantages and which is substantially cheaper than these arrangements.

These objects are attained according to the present invention in a method where the original is continuously irradiated for a predetermined period of time along a strip perpendicular to the direction in which it is continuously moved. An optical arrangement is used to break down the irradiated strip into three color-component strips which are fed to respective light-sensitive transducers which convert the color-component strips into respective multiplicities of signals each having a level corresponding to the color-component light intensity at the respective strip section. Each of these signals is stored up during the predetermined time in a memory capacitor and is fed synchronously with the copying frequency to a scriber that reproduces the color components in their respective colors on the copy sheet.

A relatively powerful light source in accordance with this invention can therefore be used which irradiates the entire strip on the copy for a predetermined period of time. Thus, much higher resolution is obtainable than in systems wherein a flying-spot scanner merely moves a light spot or electron beam over the image. Dichroic mirrors or the like can be used to break the light from the irradiated strip down into red, yellow, and green components. The elimination of the standard flying-spot scanner tube eliminates the need for a high-voltage source in the device and considerably reduces its cost and dangerousness.

In accordance with this invention the pickup device is formed of a row of photodiodes each connected to a respective capacitor that is in turn connectable through a respective gate to the output of the pickup device. A shift register controlled by a clock circuit serves for sequential reading-out of the voltages stored in the capacitors during the predetermined scanning period.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DESCRIPTION OF THE PREFERRED EMBODIMENTS

Figure 1:
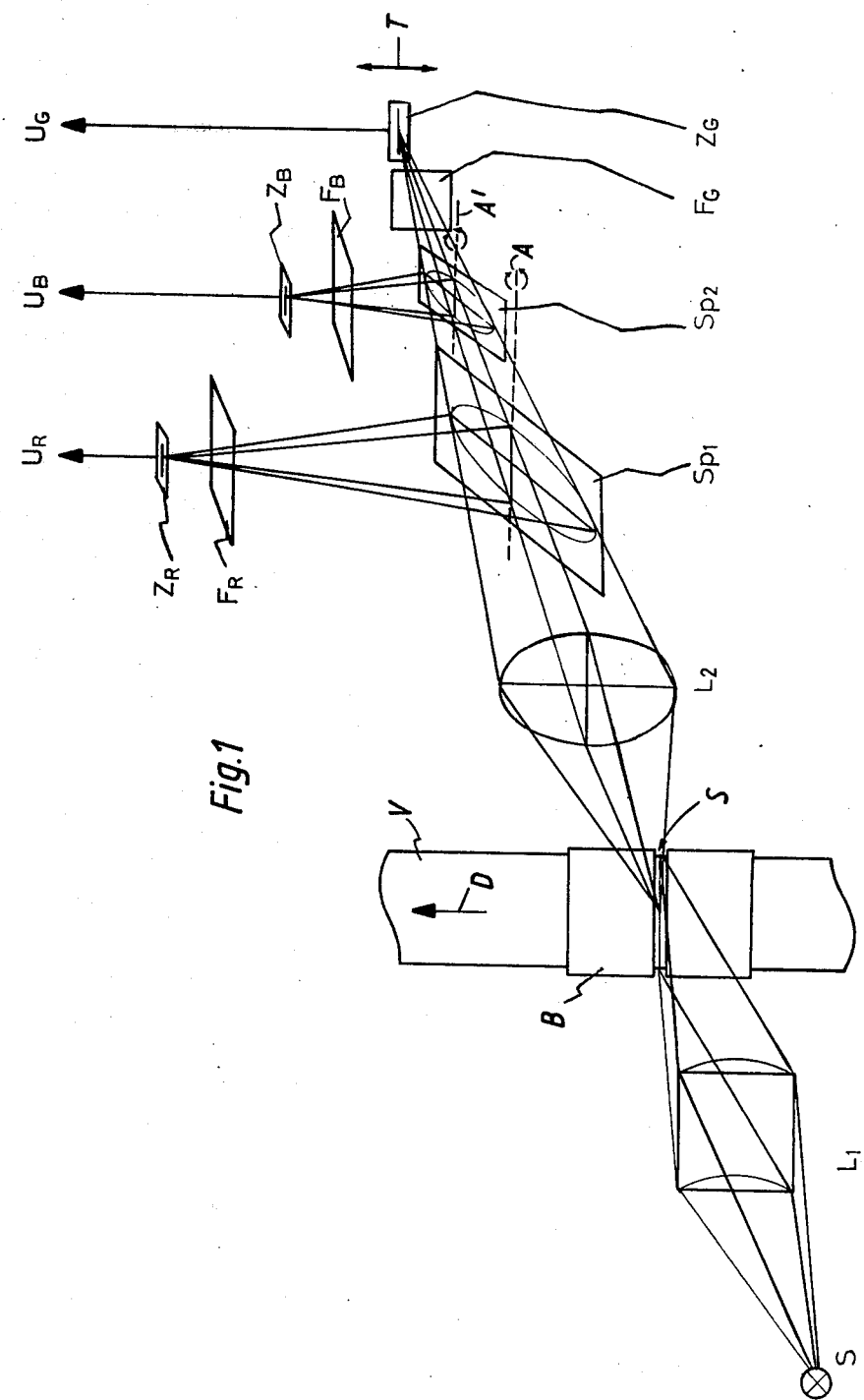
FIG. 1 is a schematic view illustrating the scanning arrangement in accordance with this invention.

As shown in FIG. 1 pure white light from a source S is focussed by means of a plano-convex bar $L_1$ onto a strip defined by a shutter B on an original V formed as a strip moving in the direction D perpendicular to the slot S defined by the shutter B. Light from the irradiated strip on the original V passes through a focussing lens $L_2$, a pair of dichroic mirrors $Sp_1$ and $Sp_2$, and a green filter $F_G$ to a green-color pickup $A_G$. The portion of light reflected by the mirror $Sp_1$ is directed through a red filter $F_R$ into a red pickup $V_R$ which produces a red output $U_R$. Similarly the light from the second dichroic mirror $Sp_2$ passes through a blue filter $F_B$ to a blue pickup $Z_B$ that produces a blue output $U_B$ similar to the red output $U_R$ of the red pickup $Z_R$ and the green output $U_G$ of the green pickup $Z_G$.

To focus on the slit F exactly, mirror $Sp_1$ is pivotal about an axis A and the mirror $Sp_2$ about an axis A' both parallel to each other and to the original V at the slot S. Similarly, the pickup $Z_G$ is displaceable parallel to the original V as indicated by double-headed arrow T.

The pickups $Z_R$, $Z_B$, and $Z_G$ are all identical. They are so-called solid-state line scanners of the self-scanning type having approximately 500 elements on 1 mil centers. A linear-array image sensor such as produced by Reticon Corporation of Mountain View, Calif. under item number RL-1024B is ideally suited to such use. Other usable devices are produced by Fairchild semiconductor under item number CCD121.A discussion of the functioning of such devices can be found in the article by James E. Carnes entitle "Charge-Coupled Imaging: State of the Art" (Conference Series No. 19: The Institute of Physics, London and Bristol, 1974).

Figure 2:
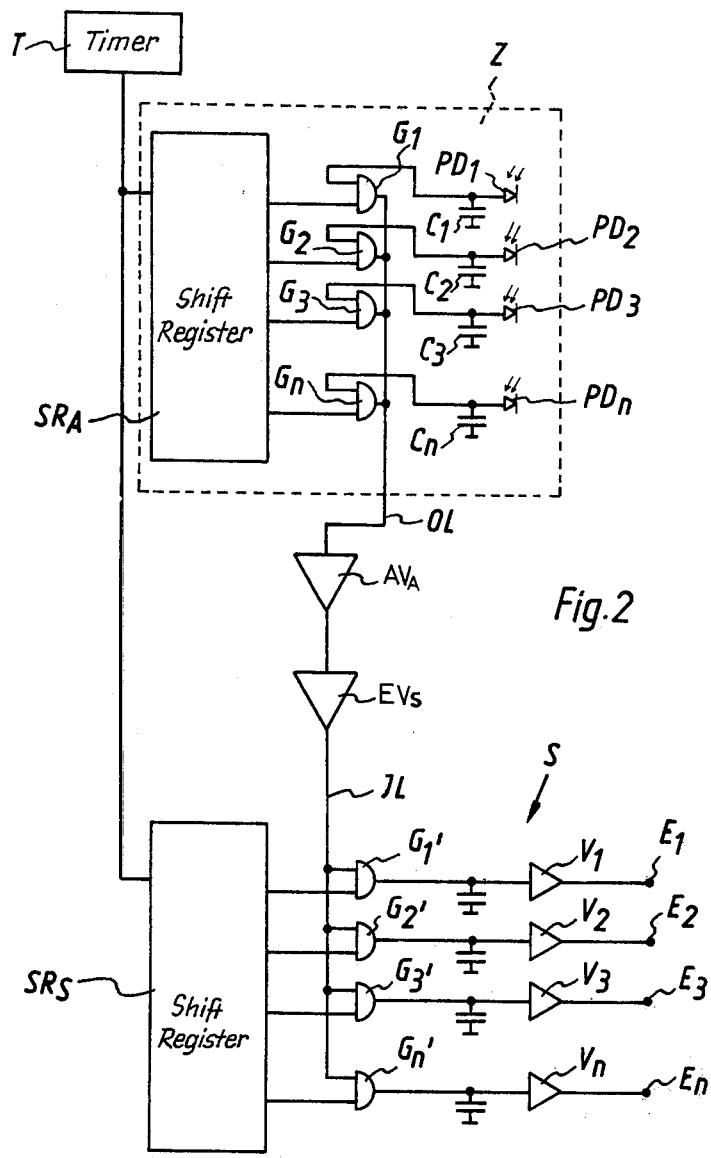
FIG. 2 is a schematic view showing a pickup and scribing arrangement in accordance with this invention.

FIG. 2 shows a typical pickup and scribing arrangement for a single color component, it being understood that each color component has an identical such pickup and scribing arrangement that operates with its own colored toner or the like on the same copy sheet. The pickup Z which is formed as a single chip as described above has a multiplicity of photodiodes $PD_1$, $PD_2$, $PD_3$ . . . $PD_n$. Each such photodiode is connected to a respective capacitor $C_1$, $C_2$, $C_3$. . . $C_n$ and to one input of a respective AND gate $G_1$, $G_2$, $G_3$. . . $G_n$ whose other inputs are all connected to a common shift register $SR_A$ and whose outputs are all connected to a common output line OL.

Each scriber S has a plurality of amplifiers $V_1$, $V_2$, $V_3$. . . $V_n$ having outputs connected to the respective electrodes $E_1$, $E_2$, $E_3$ . . . $E_n$ whose inputs are connected to respective AND gates $G'_1$, $G'_2$, $G'_3$ . . . $G'_n$ whose one inputs are all connected to a common shift register $FR_S$ and whose other inputs are all connected together to a common input line IL.

A common timer T generates clock pulses at a rate of between 10 KHz and 10 MHz. These high-frequency clock pulses are fed simultaneously to both of the shift registers $SR_a$ and $FR_S$ so as to step the respective gates synchronously. The output line OL is connected through an output amplifier $AV_A$ and an input amplifier $EV_S$ to the input line IL. The other functioning of the scriber S can be seen in the above-cited commonly assigned patent applications which are incorporated herewith by reference.

Whereas a flying-spot scanner moves over a line continuously, the row of separate photodiodes $PD_{1..n}$ automatically separates the line into discrete image points or sections. If the brightness distribution in a line varies with the frequency equal to twice the width of a picture point two possibilities can occur. The maximum sensitivity points of the meander-like brightness distribution can fall directly at the centers of the picture points with the minimum points falling directly at the centers of other picture points so that maximum contrast is obtained. Alternately, these maximum and minimum points can fall between picture points so that gray is perceived and the structure disappears altogether. Such errors occur in periodically controlled systems. Such a possibility cannot occur with the above-described system according to the present invention.

In addition, the light source shines continuously on the respective line or strip on the original V for a relatively long period of time so that high resolution is possible. Thus, the output of each photodiode is integrated by the respective capacitor for a much longer period of time than is possible with a flying-spot scanner. In an arrangement as described above where 900 picture points are provided, this increases the integration time by more than two orders of magnitude. Furthermore, the use of a solid-state semiconductor arrangement eliminates the need for a controlled 25 kilovolt power supply for the cathode ray tube and a controlled 3 kilovolt power supply for the photomultiplier thereof. In addition, an extremely long service life is obtained due to the stability of the various components.

In accordance with the present invention, a short photodiode line is employed to sense the lateral position of the original. Thus, three such arrangements as shown in FIG. 1 can be provided for reading out the separate color components, with even a fourth such system provided for a purely black signal. These arrangements are all connected to respective spaced-apart scribers as described in the above-cited commonly assigned patent applications and the short photodiode cell is used for insuring proper registration between scribing of the one color component and the next. It is possible in this arrangement to use a black-white type of pickup and to use more than three or four color components, It is also possible in accordance with this invention to immediately print one color component, store one of the other components for a period of time equal to the amount of time necessary to print the one component, then print this other component, and store the third component for twice the period of time before scribing it.

In an arrangement where three such pickups as shown in FIG. 1 are employed it is necessary to read out all three color components, as one color component cannot simple be read out and accurate results obtained.

It will be understood that each of the elements described above, or two or more together, may also find a useful application in other types of apparatus differing from the types described above.

While the invention has been illustrated and described as embodied in a color copier, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A copying method comprising the steps of:
    displacing an original in a direction past a scanning location;
    irradiating on said original at said location an entire strip extending transverse to said direction continuously for a predetermined time period;
    optically deriving during said time period a plurality of different color-component strips each corresponding to a respective color component of the irradiated strip;
    reflecting each of said color-component strips with a respective mirror during said time period to a respective transducer and simultaneously converting said color-component strips therewith into respective multiplicities of signals each corresponding to a respective section of the respective color-component strip;
    pivoting at least some of said mirrors about axes parallel to said original at said irradiated strip for focussing said mirrors on said irradiated strip;
    storing up during said time period each of said multiplicities of signals; and
    feeding after said time period each of the stored-up multiplicities of signals to respective scribers.

2. The method defined in claim 1 wherein said strip on said original is irradiated with substantially white light.

3. The method defined in claim 1 wherein said signals of said stored-up multiplicities are fed to said scribers seriatim.

4. The method defined in claim 3 wherein each of said stored-up multiplicities are each fed to said scribers signal-by-signal in accordance with the position of a copy sheet relative to the respective scribers and all the multiplicities corresponding to a single irradiated line are applied to the respective scribes when the same portion of the copy sheet positioned at the respective scriber.

5. A copying apparatus comprising:
    means for advancing an original in a predetermined direction past a scanning location;
    means for irradiating on said original at said location an entire strip extending transverse to said direction continuously for a predetermined time period;
    optical means including a plurality of dichroic mirrors at least some of which are pivotal about axes parallel to said original at said irradiated strip for deriving during said time period a plurality of different color-component strips each corresponding to a respective color component of the irradiated strip;
    circuit means for applying during said time period each of said color-component strips to a respective transducer and simultaneously converting said color component strips therewith into respective multiplicities of signals each corresponding to a respective section of the respective color-component strip;
    memory means connected to said circuit means for storing up during said time period each of said multiplicities of signals;
    a plurality of scribers; and
    feed means connected between said memory means and said scribers for feeding each of the stored-up multiplicities of signals to respective scribers.

6. The apparatus defined in claim 5, further comprising clock means connected to said optical, circuit, memory, and feed means for operating same in accordance with and for establishing said time period.

7. The apparatus defined in claim 6 wherein said memory means includes a capacitor for each of said signals.

8. The apparatus defined in claim 6 wherein said optical means includes a plurality of dichroic mirrors.

9. The apparatus defined in claim 6 wherein said circuit means includes a multiplicity of photodiodies and said memory means includes a capacitor connectable to each photodiode.

10. The apparatus defined in claim 6 wherein said feed means includes means for varying the phase said signals are applied to said scribers for proper registration of the different color components.

* * * * *